(12) United States Patent
Nagata et al.

(10) Patent No.: US 7,714,140 B2
(45) Date of Patent: May 11, 2010

(54) 1,2 BENZOISOTHIAZOLE DERIVATIVE, AND AGRICULTURAL OR HORTICULTURAL PLANT DISEASE- CONTROLLING AGENT

(75) Inventors: Toshihiro Nagata, Iwata (JP); Atsushi Kogure, Tokyo (JP); Isao Kaneko, Tokyo (JP); Norihisa Yonekura, Tokyo (JP); Ryo Hanai, Tokyo (JP)

(73) Assignees: Kumiai Chemical Industry, Co. Ltd. (JP); Ihara Chemical Industry Co., Ltd. (JP)

( * ) Notice: Subject to any disclaimer, the term of this patent is extended or adjusted under 35 U.S.C. 154(b) by 20 days.

(21) Appl. No.: 12/225,868

(22) PCT Filed: Apr. 20, 2007

(86) PCT No.: PCT/JP2007/000432

§ 371 (c)(1),
(2), (4) Date: Oct. 1, 2008

(87) PCT Pub. No.: WO2007/129454

PCT Pub. Date: Nov. 15, 2007

(65) Prior Publication Data

US 2009/0137646 A1 May 28, 2009

(30) Foreign Application Priority Data

May 8, 2006 (JP) .............................. 2006-128783

(51) Int. Cl.
*C07D 275/06* (2006.01)
*A61K 31/428* (2006.01)
(52) U.S. Cl. ...................................... 548/207; 514/373
(58) Field of Classification Search ................. 514/373; 548/207
See application file for complete search history.

(56) References Cited

U.S. PATENT DOCUMENTS 4,855,311 A 8/1989 Iriuchijima et al. ......... 514/373

FOREIGN PATENT DOCUMENTS

JP 56-133287 10/1981

OTHER PUBLICATIONS

Ung Chan Yoon, et al, "Photochemical Reactions of Pseudosaccharin Pyridinemethyl Ethers," J. Korean Chemical Society, 1997, vol. 41( 12), pp. 666-671.*
Yoon et al., "Photochemical Reactions of Pseudosaccharin Pyridinemethyl Ethers", Journal of the Korean Chemical Society, vol. 41 ,No. 12, pp. 666-671 (1997).

* cited by examiner

*Primary Examiner*—Kamel A Saeed
*Assistant Examiner*—Janet L Coppins
(74) *Attorney, Agent, or Firm*—Bacon & Thomas, PLLC

(57) ABSTRACT

A 1,2-benzoisothiazole derivative or a salt thereof is not harmful to a crop and is remarkably effective against agricultural or horticultural plant diseases such as *Pyricularia oryzae, Septoria nodorum, Pseudoperonospora cubensis* and *Colletotrichum orbiculare*, and an agricultural or horticultural plant disease-controlling agent containing the derivative or its salt as an active ingredient. The 1,2-benzoisothiazole derivative is represented by the general formula [I]:

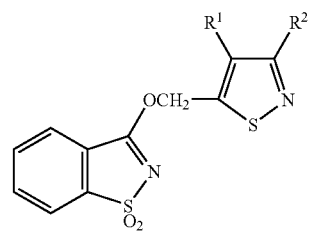

(wherein $R^1$ is a hydrogen atom or a halogen atom, and $R^2$ is a methyl group or a halogen atom), or a salt thereof.

6 Claims, No Drawings

1,2 BENZOISOTHIAZOLE DERIVATIVE, AND AGRICULTURAL OR HORTICULTURAL PLANT DISEASE- CONTROLLING AGENT

TECHNICAL FIELD

The present invention relates to a 1,2-benzoisothiazole derivative or its salt, as well as to an agricultural or horticultural plant disease-controlling agent containing the derivative or its salt as an active ingredient.

BACKGROUND ART

In cultivation of agricultural or horticultural crops, a large number of disease-controlling agents are in use for diseases of crops. However, with conventional disease-controlling agents, there are cases that the effect of disease control is insufficient or the use of controlling agent is restricted owing to the emergence of pathogenic fungi having chemical resistance; and a considerable number of conventional disease-controlling agents are not satisfactory in that they give chemical injury or stain to plants or have toxicity to men, beasts and fishes, and give adverse effects on environment. Therefore, it is strongly desired to develop a disease-controlling agent which is low in such drawbacks and can be used safely.

In Non-Patent Literature 1 is described a 3-(pyridinylmethoxy)-1,2-benzoisothiazole compound which is similar to the present compound. However, the literature makes no description on any compound in which a substituted isothiazol-5-ylmethyl group is bonded to the 3-position of 1,2-benzoisothiazole ring via an oxygen atom, or on any agricultural or horticultural plant disease-controlling agent.

In Patent Literature 1 is described, as a specific example, a 3-(pyridin-4-ylmethoxy)-1,2-benzoisothiazole derivative which is similar to the present compound. In the literature, however, there is no description of a compound in which a substituted isothiazol-5-ylmethyl group is bonded to the 3-position of 1,2-benzoisothiazole ring via an oxygen atom. The literature further describes the 1,2-benzoisothiazole derivative as a plant disease-controlling agent, however, the disease-controlling effect thereof is not satisfactory.

Non-Patent Literature 1: Journal of the Korean Chemical Society, Vol. 41, p. 666, (1997)
Patent Literature 1: JP-A-1981-133287

DISCLOSURE OF THE INVENTION

Task to be Achieved by the Invention

The task of the present invention is to solve the above-mentioned problems of conventional plant disease-controlling agents and further provide a plant disease-controlling agent which is superior in controlling effect, residual activity, etc.

Means for Achieving the Task

In order to achieve the above task, the present inventors synthesized a large number of 1,2-benzoisothiazole derivatives whose plant disease-controlling activities were unknown, and investigated their plant disease-controlling activities and usefulnesses. As a result, it was found that the 1,2-benzoisothiazole derivative of the present invention (hereinafter referred to as the present invention compound) or its salt, when applied to plants, shows a plant disease-controlling activity over a long period and gives a striking plant disease-controlling effect to plants with no chemical injury thereto. The finding has led to the completion of the present invention.

The present invention relates to the following (1) to (4).

(1) A 1,2-benzoisothiazole derivative represented by the general formula [I]

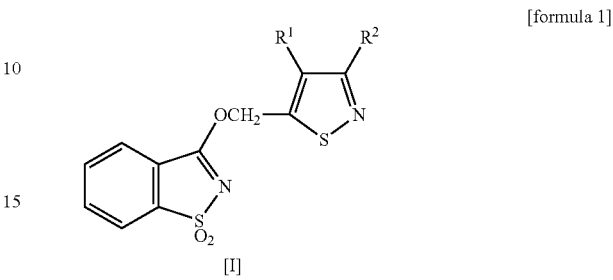

[formula 1]

(wherein $R^1$ is a hydrogen atom or a halogen atom, and $R^2$ is a methyl group or a halogen atom), or a salt thereof.

(2) A 1,2-benzoisothiazole derivative or a salt thereof according to (1), wherein $R^1$ is a hydrogen atom, a chlorine atom or a bromine atom, and $R^2$ is a methyl group, a chlorine atom or a bromine atom.

(3) A 1,2-benzoisothiazole derivative or a salt thereof according to (1), wherein $R^1$ is a chlorine atom or a bromine atom, and $R^2$ is a chlorine atom or a bromine atom.

(4) An agricultural or horticultural plant disease-controlling agent containing, as an active ingredient, a 1,2-benzoisothiazole derivative or a salt thereof according to (1) to (3).

EFFECT OF THE INVENTION

The agricultural or horticultural plant disease-controlling agent of the present invention is characterized by giving no chemical injury to crops and showing high controlling effects to rice blast disease, wheat glume blotch, cucumber downy mildew, cucumber anthracnose, etc.; therefore, it is useful as an agricultural or horticultural plant disease-controlling agent.

BEST MODE FOR CARRYING OUT THE INVENTION

Next, specific examples of the present invention compound represented by the general formula [I] are indicated in Table 1. However, the present invention compound is not restricted to these compounds. Incidentally, the compound Nos. shown in Table 1 are used in the later description.

TABLE 1

| Compound No. | $R^1$ | $R^2$ |
|---|---|---|
| 1 | Cl | Cl |
| 2 | Br | Br |
| 3 | Br | Cl |

TABLE 1-continued

| Compound No. | R¹ | R² |
|---|---|---|
| 4 | Cl | Br |
| 5 | H | Me |

A representative method for production of the present invention compound is illustrated below. However, the production method of the present invention compound is not restricted thereto.

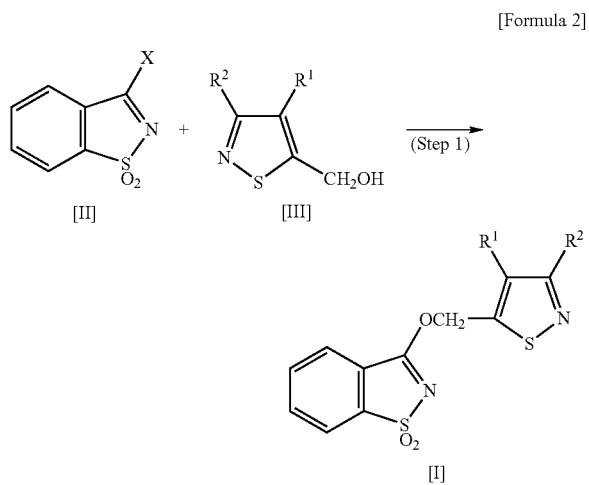

[Formula 2]

(wherein X is a halogen atom such as chlorine atom, bromine atom or the like, and $R^1$ and $R^2$ have the same definitions as given above.)

(Step 1)

The present invention compound represented by the general formula [I] can be produced by reacting a 3-halogeno-1,2-benzoisothiazole 1,1-dioxide represented by the general formula [II] with a compound represented by the general formula [III] in the presence or absence of a base in a solvent or in the absence of a solvent (hereinafter, for example, "compound represented by the general formula [III]" and "compound [III]" have the same meaning).

Incidentally, the compound [II] used in the present step can be produced from saccharin according to the method described in Synlett, 1997, No. 12, p. 1355.

The use amount of the compound [III] can be appropriately selected in a range of 0.5 to 10 mols relative to 1 mol of the compound [II] and is preferably 0.8 to 1.2 mols.

As the base usable in the present step, there can be mentioned, for example, metal carbonates such as sodium carbonate, potassium carbonate and the like; metal hydrogencarbonates such as sodium hydrogencarbonate, potassium hydrogencarbonate and the like; carboxylic acid salts such as sodium acetate, potassium acetate and the like; metal alkoxides such as sodium methoxide, sodium ethoxide, potassium tert-butoxide and the like; metal hydroxides such as sodium hydroxide, potassium hydroxide, calcium hydroxide and the like; metal hydrides such as sodium hydride, potassium hydride, calcium hydride and the like; and organic bases such as triethylamine, N,N-diisopropylethylamine, pyridine, 1,8-diazabicyclo[5.4.0]undec-7-ene (DBU) and the like.

The use amount of the base can be appropriately selected in a range of 0 to 10 mols relative to 1 mol of the compound [III] and is preferably 0 to 1.2 mols.

The solvent usable in the present reaction may be any solvent as long as it does not inhibit the progress of the present reaction. There can be used, for example, ethers such as diethyl ether, tetrahydrofuran (THF), dioxane, monoglyme, diglyme and the like; halogenated hydrocarbons such as dichloromethane, chloroform, carbon tetrachloride, dichloroethane and the like; aromatic hydrocarbons such as benzene, chlorobenzene, nitrobenzene, toluene, xylene and the like; amides such as N,N-dimethylformamide (DMF), N,N-dimethylacetamide and the like; ureas such as 1,3-dimethyl-2-imidazolidinone and the like; sulfur compounds such as dimethyl sulfoxide and the like; and nitrites such as acetonitrile and the like. Mixed solvents thereof can also be used.

The reaction temperature may be selected in a range from −20° C. to the boiling point of the solvent used and is preferably in a range of 0 to 50° C.

The reaction time differs depending upon the reaction temperature, the reaction substrate, the scale of reaction, etc., but is ordinarily 30 minutes to 48 hours.

The present invention compound represented by the general formula [I], which is an intended product of reaction, is obtained from the reaction system after the completion of the reaction, according to an ordinary method. The intended product obtained may be purified as necessary by an operation such as column chromatography, recrystallization or the like.

Meanwhile, the compound [III] used in the present step can be produced by the following method.

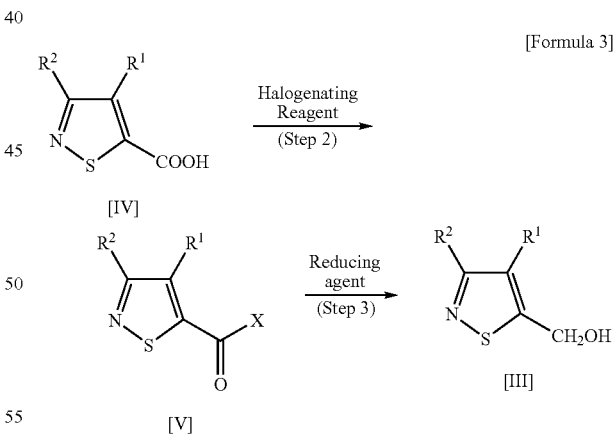

[Formula 3]

(wherein X, $R^1$ and $R^2$ have the same definitions as given above.)

(Step 2)

The compound represented by the general formula [V] can be produced by reacting a compound represented by the general formula [IV] with a halogenating reagent in a solvent or in the absence of a solvent.

As the halogenating reagent used in the present step, there can be mentioned, for example, an acid halide such as oxalyl chloride, thionyl chloride or the like. As necessary, an amide such as N,N-dimethylformamide or the like may be added in a catalytic amount.

The use amount of the halogenating reagent may be selected appropriately in a range of 1 to 100 mols relative to 1 mol of the compound represented by the general formula [IV] and is preferably 1 to 5 mols.

The solvent usable in the present reaction may be any solvent as long as it does not inhibit the progress of the present reaction. There can be used, for example, ethers such as diethyl ether, tetrahydrofuran, dioxane, monoglyme, diglyme and the like; halogenated hydrocarbons such as dichloromethane, chloroform, carbon tetrachloride, dichloroethane and the like; aromatic hydrocarbons such as benzene, chlorobenzene, nitrobenzene, toluene, xylene and the like; and nitrites such as acetonitrile and the like. Mixed solvents thereof can also be used.

The use amount of the solvent is 0 to 100 liters relative to 1 mol of the compound represented by the general formula [IV] and is preferably 0 to 2.0 liters.

The reaction temperature may be selected in a range from −20° C. to the boiling point of the inert solvent used and is preferably in a range of 0 to 100° C.

The reaction time differs depending upon the reaction temperature, the reaction substrate, the scale of reaction, etc., but is ordinarily 30 minutes to 10 hours.

The compound represented by the general formula [V] is obtained from the reaction system after the completion of the reaction, according to an ordinary method and may be purified as necessary by an operation such as column chromatography, recrystallization or the like.

(Step 3)

The compound represented by the general formula [III] can be produced by reacting a compound represented by the general formula [V] with a reducing agent in a solvent or in the absence of a solvent.

As the reducing agent usable in the present step, there can be mentioned, for example, boron hydride compounds such as sodium borohydride and the like.

The use amount of the reducing agent may be appropriately selected in a range of 1 to 100 mols relative to 1 mol of the compound represented by the general formula [V] and is preferably 1 to 5 mols.

The solvent usable in the present reaction may be any solvent as long as it does not inhibit the progress of the present reaction. There can be used, for example, ethers such as diethyl ether, tetrahydrofuran, dioxane, monoglyme, diglyme and the like; alcohols such as methanol, ethanol, propanol, isopropanol, butanol, tert-butanol and the like; halogenated hydrocarbons such as dichloromethane, chloroform, carbon tetrachloride, dichloroethane and the like; aromatic hydrocarbons such as benzene, chlorobenzene, nitrobenzene, toluene, xylene and the like; amides such as N,N-dimethylformamide, N,N-dimethylacetamide and the like; ureas such as 1,3-dimethyl-2-imidazolidinone and the like; sulfur compounds such as dimethyl sulfoxide and the like; nitrites such as acetonitrile and the like; and water. Mixed solvents thereof can also be used.

The use amount of the solvent is 0 to 100 liters relative to 1 mol of the compound represented by the general formula [V] and is preferably 0.1 to 2.0 liters.

The reaction temperature may be selected in a range from −20° C. to the boiling point of the inert solvent used and is preferably in a range of 0 to 100° C.

The reaction time differs depending upon the reaction temperature, the reaction substrate, the scale of reaction, etc., but is ordinarily 10 minutes to 10 hours.

The compound represented by the general formula [III] is obtained from the reaction system after the completion of the reaction, according to an ordinary method and may be purified as necessary by an operation such as column chromatography, recrystallization or the like.

The agricultural or horticultural plant disease-controlling agent of the present invention contains, as an active ingredient, a benzoisothiazole derivative represented by the general formula [I] or its salt.

In using the present invention compound as an agricultural or horticultural plant disease-controlling agent, the compound may be used per se; however, by adding thereto a carrier, a surfactant and other auxiliary agent, all used generally as an auxiliary substance in production of agricultural chemical, the compound can be prepared in various formulations of different forms such as emulsifiable concentrate, suspension concentrate, dust, granule, tablet, wettable powder, water-soluble powder, liquid formulation, flowable, water dispersible granule, aerosol, paste, oil solution, emulsion, smoking agent and the like. The proportion of the auxiliary substance added is ordinarily 10 to 99.9% by weight relative to 0.1 to 90% by weight of the active ingredient.

The carrier used in preparation of formulation includes a solid carrier and a liquid carrier. As the solid carrier, there can be mentioned, for example, animal- or plant-derived powders such as starch, active carbon, soybean flour, wheat flour, wood flour, fish meal, milk powder and the like; and inorganic powders such as talc, kaolin, bentonite, calcium carbonate, zeolite, diatomaceous earth, white carbon, clay, alumina, vermiculite, silica sand, ammonium sulfate, urea and the like. As the liquid carrier, there can be mentioned, for example, water; alcohols such as isopropyl alcohol, ethylene glycol and the like; ketones such as cyclohexanone, methyl ethyl ketone, isophorone and the like; ethers such as dioxane, tetrahydrofuran and the like; aliphatic hydrocarbons such as kerosene, gas oil and the like; aromatic hydrocarbons such as xylene, trimethylbenzene, tetramethylbenzene, methylnaphthalene, solvent naphtha and the like, halogenated hydrocarbons such as chlorobenzene and the like; acid amides such as dimethylacetamide and the like; esters such as glycerine ester of fatty acid and the like; nitrites such as acetonitrile and the like; and sulfur compounds such as dimethyl sulfoxide and the like:

As the surfactant, there can be mentioned, for example, metal alkylbenzenesulfonate, metal dinaphthylmethanedisulfonate, salt of alcohol sulfate, alklarylsulfonic acid salt, ligninsulfonic acid salt, polyoxyethylene glycol ether, polyoxyethylene alkyl aryl ether, polyoxyethylene sorbitan monoalkylate, and salt of naphthalenesulfonic acid-formalin condensate.

As the other auxiliary agent, there can be used, for example, sticking agents or thickening agents such as carboxymethyl cellulose, gum arabic, sodium alginate, guar gum, tragacanth gum, polyvinyl alcohol and the like; antifoaming agents such as metal soap and the like; property improvers such as fatty acid, alkyl phosphate salt, silicone, paraffin and the like; and coloring agents.

The agricultural or horticultural plant disease-controlling agent of the present invention may further contain as necessary, in various formulation forms mentioned above, known active compounds other than the active ingredient (the present invention compound), such as insecticide, acaricide, insect growth-controlling agent, nematicide, fungicide, plant disease-controlling agent, herbicide, plant growth-controlling agent, fertilizer, soil improver and the like.

Each formulation of the agricultural or horticultural plant disease-controlling agent of the present invention can be used per se or after dilution by, for example, foliage spraying, seed treatment, soil application, submerged application or application in nursery box. The application amount thereof varies depending upon the kind of the compound used, the disease of target, the tendency of infestation, the degree of damage, the condition of environment, the kind of formulation used, etc.

For example, in the case of dust or granule which is used per se, the use amount is appropriately selected so that the active ingredient becomes 0.1 g to 5 kg, preferably 1 g to 1 kg per 10 ares.

In the case of emulsifiable concentrate or wettable powder which is used in a liquid state, the use amount is appropriately selected so that the active ingredient becomes 0.1 ppm to 10,000 ppm, preferably 10 to 3,000 ppm.

In the case of application into nursery box, a controlling agent is prepared in a form in which the dissolution of active ingredient is controlled, whereby the agent can show an effect over a long period.

By being applied in the above-mentioned forms, the agricultural or horticultural plant disease-controlling agent of the present invention can control plant diseases caused by fungi, bacteria, viruses, etc.

Next, specific diseases are mentioned as non-restrictive examples.

*Pseudoperonospora cubensis, Venturia inaequalis, Sphaerotheca cucurbitae, Erysiphe graminis, Septoria nodorum, Pyricularia oryzae, Botrytis cinerea, Rhizoctonia solani, Puccinia recondita, Pseudomonas syringe, Xanthomonas oryzae, Burkholderia glumae, Burkholderia plantarii, Acidovorax avenae, Erwinia ananas, Colletotrichum orbiculare*

EXAMPLES

The method for producing the benzoisothiazole derivative represented by the general formula [I], used in the agricultural or horticultural plant disease-controlling agent of the present invention, and the method for preparing the controlling agent are described below in detail, in the following Examples. However, the present invention is in no way restricted by these Examples. Incidentally, in the following description, "%" is based on weight.

Example 1

Production of 3-(3,4-dichloroisothiazol-5-yl-methoxy)-1,2-benzoisothiazole 1,1-dioxide (Present Invention Compound No. 1)

To 4.0 g (20.3 mmol) of 3,4-dichloroisothiazole-5-carboxylic acid were added 8 ml of oxalyl chloride and a catalytic amount of DMF, followed by stirring at 50° C. for 30 minutes to give rise to a reaction. The reaction mixture was concentrated under vacuum to obtain 3,4-dichloroisothiazole-5-carbonyl chloride.

1.9 g (50.5 mmol) of sodium borohydride was suspended in 40 ml of water. To the resulting suspension was dropwise added, at 10 to 15° C., a solution of the 3,4-dichloroisothiazole-5-carbonyl chloride dissolved in THF (4 ml). Stirring was conducted at 15° C. for 30 minutes. Then, an aqueous citric acid solution was added to make the mixture weakly acidic and extraction with ethyl acetate was conducted. The organic layer was washed with water, dried over anhydrous magnesium sulfate, and concentrated. The resulting crystals were washed with hexane to obtain 3.0 g (yield: 81%) of (3,4-dichloroisothiazol-5-yl)methanol as colorless crystals (melting point: 94 to 95° C.).

$^1$H-NMR (CDCl$_3$) δ: 2.28 (1H, bs), 4.96 (2H, s) ppm

In 6 ml of acetonitrile were dissolved 0.62 g (3.10 mmol) of 3-chloro-1,2-benzoisothiazole 1,1-dioxide and 0.57 g (3.10 mmol) of the (3,4-dichloroisothiazol-5-yl)methanol. To the resulting solution was dropwise added 0.34 g (3.4 mmol) of triethylamine, followed by stirring at room temperature for 5 hours to give rise to a reaction. After the completion of the reaction, 12 ml of water was added. The resulting crystals were obtained by filtration. The crystals were washed with water and isopropyl alcohol to obtain 0.89 g (yield: 82%) of 3-(3,4-dichloroisothiazol-5-ylmethoxy)-1,2-benzoisothiazole 1,1-dioxide as a colorless powder (melting point: 165 to 167° C.).

$^1$H-NMR (CDCl$_3$) δ: 5.79 (2H, s), 7.73-7.94 (4H, m) ppm

Example 2

Production of 3-(3-methylisothiazol-5-ylmethoxy)-1,2-benzoisothiazole 1,1-dioxide (present invention compound No. 5)

In 8 ml of acetonitrile were dissolved 0.78 g (3.88 mmol) of 3-chloro-1,2-benzoisothiazole 1,1-dioxide and 0.50 g (3.88 mmol) of (3-methylisothiazol-5-yl)methanol. To the resulting solution was dropwise added 0.51 g (5.0 mmol) of triethylamine, followed by stirring at room temperature for 5 hours to give rise to a reaction. After the completion of the reaction, 16 ml of water was added. The resulting crystals were obtained by filtration and washed with water and isopropyl alcohol to obtain 0.30 g (yield: 26%) of 3-(3-methylisothiazol-5-ylmethoxy)-1,2-benzoisothiazole 1,1-dioxide as a light brown powder (melting point: 202 to 204° C.)

$^1$H-NMR (CDCl$_3$) δ: 2.53 (3H, s), 5.82 (2H, s), 7.15 (1H, s), 7.70-7.93 (4H, m) ppm Next, the method for preparation of controlling agent is specifically described on representative controlling agents. The kinds of compound and additives, and the compounding ratio thereof are not restricted to those shown below and can be varied in wide ranges. In the following description, "parts" refer to parts by weight.

Example 3

Dust

| Compound No. 1 | 2 parts |
| --- | --- |
| Diatomaceous earth | 5 parts |
| Clay | 93 parts |

The above substances were uniformly mixed and ground to obtain a dust. The compound No. 1 was replaced by other compounds shown in Table 1, whereby dusts could be obtained in the same manner.

Example 4

Wettable Powder

| | |
|---|---|
| Compound No. 1 | 50 parts |
| Diatomaceous earth | 45 parts |
| Sodium dinaphthylmethanedisulfonate | 2 parts |
| Sodium ligninsulfonate | 3 parts |

The above substances were uniformly mixed and ground to obtain a wettable powder. The compound No. 1 was replaced by other compounds shown in Table 1, whereby wettable powders could be obtained in the same manner.

Example 5

Wettable Powder

| | |
|---|---|
| Compound No. 1 | 10 parts |
| Clay | 69 parts |
| Diatomaceous earth | 20 parts |
| Sodium salt of β-naphthalenesulfonic acid-formalin condensate | 0.5 part |
| Polyoxyethylene octyl phenyl ether | 0.5 part |

The above substances were uniformly mixed and ground to obtain a wettable powder. The compound No. 1 was replaced by other compounds shown in Table 1, whereby wettable powders could be obtained in the same manner.

Example 6

Emulsifiable Concentrate

| | |
|---|---|
| Compound No. 1 | 30 parts |
| Cyclohexanone | 20 parts |
| Polyoxyethylene alkyl aryl ether | 11 arts |
| Calcium alkylbenzenesulfonate | 4 parts |
| Methylnaphthalene | 35 parts |

The above substances were uniformly dissolved to obtain an emulsifiable concentrate. The compound No. 1 was replaced by other compounds shown in Table 1, whereby emulsifiable concentrates could be obtained in the same manner.

Example 7

Granule

| | |
|---|---|
| Compound No. 1 | 4 parts |
| Sodium salt of lauryl alcohol sulfate | 2 parts |
| Sodium ligninsulfonate | 5 parts |
| Carboxymethyl cellulose | 2 parts |
| Clay | 87 parts |

The above substances were uniformly mixed and ground. Thereto was added 20 parts of water, followed by kneading. The kneaded product was processed into granular materials of 14 to 32 meshes using an extruding granulator, followed by drying, to obtain granule. The compound No. 1 was replaced by other compounds shown in Table 1, whereby granules could be obtained in the same manner.

Next, the effect shown by the agricultural or horticultural plant disease-controlling agent of the present invention is specifically described by way of Test Examples.

Test Example 1

Test of Root Treatment at Transplanting, for Rice Blast Disease

A wettable powder prepared according to Example 5 was diluted with water so that the concentration of active ingredient became 30 g per 10 ares. 250 μl of the resulting chemical solution was applied to the root of paddy rice plant of 3-leaf stage (variety: Aichi Asahi). 2 hours later, the paddy rice was transplanted into a white porcelain basin of 9 cm in diameter (each three paddy rice plants were trans-planted at four different places), and was grown in a greenhouse. 26 days after the treatment, a conidia suspension of *Pyricularia oryzae* was inoculated by spraying; immediately, the basin was placed in a moist chamber of 25° C. for 24 hours. Then, the basin was transferred into the greenhouse and, 8 days after the inoculation, the number of lesions on the leaf which had been latest at the inoculation, was examined. A protective value was calculated from the following mathematical expression and evaluated according to the standard of table 2. The result is shown in Table 3.

Protective value=[1−(the number of lesions in treated plants)/(the number of lesions in untreated plants)]×100    [Expression 1]

TABLE 2

| Evaluation |
|---|
| A: protective value: 100% to 90.0% or more |
| B: protective value: less than 90.0% to 80.0% or more |
| C: protective value: less than 80.0% to 50.0% or more |
| D: protective value: less than 50.0% |

Using a comparative compound shown below, a wettable powder was prepared according to Example 5. A control number thereof was calculated in the same manner as in the above Test Example. The result is shown in Table 3.

TABLE 3

[Formula 4]

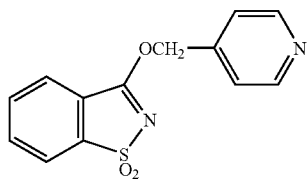

Comparative Compound 1

(Described in Non-Patent Literature 1 and Patent Literature 1)

| Compound No. | Evaluation |
| --- | --- |
| 1 | B |
| 5 | B |
| Comparative compound 1 | C |
| Control compound Probenazole | C |

Test Example 2

Test for Preventive Effect for Cucumber Anthracnose

Four cucumber seeds (variety: Sagamihanjiro) were sowed in a plastic cup of 5.5 cm in diameter, at a depth of 2 cm, and were grown in a greenhouse for 7 days. A wettable powder prepared according to Example 5 was diluted with water so that the concentration of active ingredient became a given level. 10 ml of the dilution was poured into the soil at the root of young cucumber seedlings having cotyledons. 7 days later, a conidia suspension ($10^5$ to $10^6$/ml) of *Colletotrichum orbiculare* which had been cultured in a PDA plate medium, was uniformly inoculated to the cucumber plant by hand spraying. The cup was allowed to stand in a moist chamber of 25° C. for 24 hours. Then, the cup was allowed to stand on a basin in a glass greenhouse and, 7 day later, the number of lesions of all cotyledons in pot was examined. A protective value was calculated from the expression 1 and evaluated according to the standard of Table 2. The result is shown in Table 4.

Using a comparative compound shown below, a wettable powder was prepared according to Example 5. A control number thereof was calculated in the same manner as in the above Test Example. The result is shown in Table 4.

TABLE 4

[Formula 5]

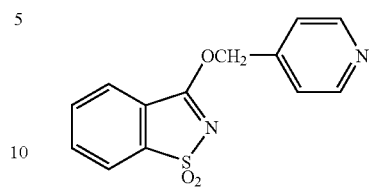

Comparative Compound 1

(Described in Non-Patent Literature 1 and Patent Literature 1)

| Compound No. | Concentration of active ingredient (ppm) | Evaluation |
| --- | --- | --- |
| 1 | 10 | A |
|   | 1  | A |
| 5 | 10 | A |
|   | 1  | D |
| Comparative compound 1 | 10 | B |
|   | 1  | D |

The invention claimed is:

1. A 1,2-benzoisothiazole derivative represented by the general formula [I]

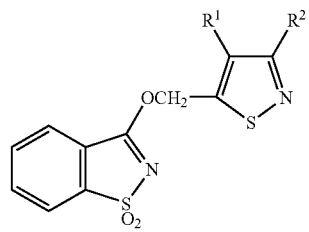

[I]

(wherein $R^1$ is a hydrogen atom or a halogen atom, and $R^2$ is a methyl group or a halogen atom), or a salt thereof.

2. A 1,2-benzoisothiazole derivative or a salt thereof according to claim 1, wherein $R^1$ is a hydrogen atom, a chlorine atom or a bromine atom, and $R^2$ is a methyl group, a chlorine atom or a bromine atom.

3. A 1,2-benzoisothiazole derivative or a salt thereof according to claim 1, wherein $R^1$ is a chlorine atom or a bromine atom, and $R^2$ is a chlorine atom or a bromine atom.

4. An agricultural or horticultural plant disease-controlling agent containing, as an active ingredient, a 1,2-benzoisothiazole derivative or a salt thereof according to claim 3.

5. An agricultural or horticultural plant disease-controlling agent containing, as an active ingredient, a 1,2-benzoisothiazole derivative or a salt thereof according to claim 1.

6. An agricultural or horticultural plant disease-controlling agent containing, as an active ingredient, a 1,2-benzoisothiazole derivative or a salt thereof according to claim 2.

* * * * *